US008450085B2

(12) United States Patent
Montelione et al.

(10) Patent No.: US 8,450,085 B2
(45) Date of Patent: May 28, 2013

(54) LABELED BIOMOLECULAR COMPOSITIONS AND METHODS FOR THE PRODUCTION AND USES THEREOF

(75) Inventors: Gaetano T. Montelione, Highland Park, NJ (US); Masayori Inouye, New Brunswick, NJ (US); Yuefeng Tang, Highland Park, NJ (US); Monica Roth, New York, NY (US); William Schneider, Hamilton, NJ (US)

(73) Assignees: University of Medicine and Dentistry of New Jersey, Somerset, NJ (US); Rutgers, The State University of New Jersey, New Brunswick, NJ (US)

( * ) Notice: Subject to any disclaimer, the term of this patent is extended or adjusted under 35 U.S.C. 154(b) by 325 days.

(21) Appl. No.: 12/531,447

(22) PCT Filed: Mar. 17, 2008

(86) PCT No.: PCT/US2008/057267
§ 371 (c)(1),
(2), (4) Date: Apr. 27, 2010

(87) PCT Pub. No.: WO2008/115887
PCT Pub. Date: Sep. 25, 2008

(65) Prior Publication Data
US 2010/0228009 A1    Sep. 9, 2010

Related U.S. Application Data

(60) Provisional application No. 60/918,418, filed on Mar. 16, 2007.

(51) Int. Cl.
*C12P 21/06* (2006.01)
(52) U.S. Cl.
USPC ......................................................... 435/69.1
(58) Field of Classification Search
None
See application file for complete search history.

(56) References Cited

U.S. PATENT DOCUMENTS 5,849,576 A *  12/1998  Skerra et al. ................ 435/320.1
7,985,575 B2 *   7/2011  Inouye et al. ............. 435/252.33

OTHER PUBLICATIONS

Written Opinion of the International Searching Authority for PCT/US2008/057267, dated Aug. 30, 2008.
International Search Report for PCT/US2008/057267, dated Aug. 30, 2008.
International Preliminary Report on Patentability for PCT/US2008/057267, dated Dec. 7, 2009.
Acton, et al. (2005). Robotic Cloning and Protein Production Platform of the Northeast Structural Genomics Consortium. Methods Enzymol 394, 210-243.
Arora, et al. (2001). Structure of outer membrane protein A transmembrane domain by NMR spectroscopy. Nat Struct Biol 8, 334-338.
Astrof, et al. (2001). Triple resonance solid state NMR experiments with reduced dimensionality evolution periods. J Magn Reson 152, 303-307.
Castellani, et al. (2002). Structure of a protein determined by solid-state magicangle-spinning NMR spectroscopy. Nature 420, 98-102.
Castellani, et al. (2003). Determination of solid-state NMR structures of proteins by means of three-dimensional 15N-J3C-J3C dipolar correlation spectroscopy and chemical shift analysis. Biochemistry 42, 11476-11483.
De Angelis, et al. (2006). Structure determination of a membrane protein with two trans-membrane helices in aligned phospholipid bicelles by solid-state NMR spectroscopy. J Am Chem Soc 128, 12256-12267.
Drechsler, et al. (2003). Solid-state NMR structure determination. IUBMB Life 55, 515-523.
Fernandez, et al. (2002). Lipid-protein interactions in DHPC micelles containing the integral membrane protein OmpX investigated by NMR spectroscopy. Proc Natl Acad Sci USA 99, 13533-13537.
Fernandez, et al. (2003). NMR solution structure determination of membrane proteins reconstituted in detergent micelles. FEBS Lett 555, 144-150.
Fernandez, et al. (2004). NMR structure of the integral membrane protein OmpX. J Mol Biol 336, 1211-1221.
Gardner, et al. (1997). Global folds of highly deuterated, methyl-protonated proteins by multidimensional NMR. Biochemistry 36, 1389-1401.
Huang, et al. (2005). An integrated platform for automated analysis of protein NMR structures. Methods Enzymol 394, 111-141.
Huang, et al. (2006). A topology-constrained distance network algorithm for protein structure determination from NOESY data. Proteins 62, 587-603.
Igumenova, et al. (2004a). Assignments of carbon NMR resonances for microcrystalline ubiquitin. J Am Chem Soc 126, 6720-6727.
Igumenova, et al. (2004b). Assignment of the backbone resonances for microcrystalline ubiquitin. J Am Chem Soc 126, 5323-5331.
Jansson, et al. (1996). High-level production of uniformly 15N- and 13C-enriched fusion proteins in *Escherichia coli*. J Biomol NMR 7, 131-141.
Jaroniec, et al. (2004). High-resolution molecular structure of a peptide in an amyloid fibril determined by magic angle spinning NMR spectroscopy. Proc Natl Acad Sci USA 101, 71 1-716.
Kennedy, et al. (2002). Role for NMR in structural genomics. J Struct Funct Genomics 2, 155-169.
Kim, et al. (2001). Complete cross-validation and R-factor calculation of a solid-state NMR derived structure. J Am Chem Soc 123, 7292-7298.
Krabben, et al. (2004). Towards structure determination of neurotoxin II bound to nicotinic acetylcholine receptor: a solid-state NMR approach. FEBS Left 564, 319-324.

(Continued)

*Primary Examiner* — Nashaat Nashed
(74) *Attorney, Agent, or Firm* — Fox Rothschild LLP

(57) ABSTRACT

Disclosed herein is a set of *E. coli* single-protein production (SPP) technologies with protein NMR (SPP-NMR) for (i) using isotope-enriched membrane proteins produced with the SPP system in screening detergent conditions suitable for purification and/or three-dimensional structure analysis without the requirement for protein purification, (ii) producing $^2$H, $^{13}$C, $^{15}$N enriched proteins suitable for high throughput and membrane protein NMR studies, and (iii) labeling with $^{13}$C—$^{15}$N specific peptide bonds in proteins (referred to herein as SPP-PBL).

9 Claims, 12 Drawing Sheets

OTHER PUBLICATIONS

Krueger-Koplin, et al. (2004). An evaluation of detergents for NMR structural studies of membrane proteins. J Biomol NMR 28, 43-57.

Marassi, et al. (2002). Using pisa pies to resolve ambiguities in angular constraints from PISEMA spectra of aligned proteins. J Biomol NMR 23, 239-242.

Marassi, et al. (2003). Simultaneous assignment and structure determination of a membrane protein from NMR orientational restraints. Protein Sci 12, 403-411.

Montelione. (2001). Structural genomics: an approach to the protein folding problem. Proc Natl Acad Sci USA 98, 13488-13489.

Moseley, et al. (1999). Automated analysis of NMR assignments and structures for proteins. Curr Opin Struct Biol 9, 635-642.

Moseley, et al. (2001). Automatic determination of protein backbone resonance assignments from triple resonance nuclear magnetic resonance data. Methods Enzymol 339, 91-108.

Opella. (2003). Membrane protein NMR studies. Methods Mol Biol 227, 307-320.

Park, et al. (2003). Three-dimensional structure of the channel-forming trans-membrane domain of virus protein "u" (Vpu) from HIV-I. J Mol Biol 333, 409-424.

Petkova, et al. (2003). Backbone and side chain assignment strategies for multiply labeled membrane peptides and proteins in the solid state. J Magn Reson 160, 1-12.

Rienstra, et al. (2002). De novo determination of peptide structure with solid-state magic-angle spinning NMR spectroscopy. Proc Nat. Acad Sci USA 99, 10260-10265.

Shan, et al. (1998). Subunit-specific backbone NMR assignments of a 64 kDa trp repressor/DNA complex: a role for N-terminal residues in tandem binding. J Biomol NMR 11, 307-318.

Sorgen, et al. (2002a). Structure of the *Rhodobacter sphaeroides* light-harvesting 1 beta subunit in detergent micelles. Biochemistry 41, 31-41.

Sorgen, et al. (2002b). An approach to membrane protein structure without crystals. Proc Natl Acad Sci USA 99, 14037-14040.

Suzuki, et al. (2005). Single protein production in living cells facilitated by an mRNA interferase. Mol Cell 18, 253-261.

Suzuki, et al. (2006). Bacterial bioreactors for high yield production of recombinant protein. J Biol Chem 281, 37559-37565.

Tamm, et al. (2003). Structure, dynamics and function of the outer membrane protein A (OmpA) and influenza hemagglutinin fusion domain in detergent micelles by solution NMR. FEBS Lett 555, 139-143.

Valentine, et al. (2003). Structure, topology, and dynamics of myristoyluled recoverin bound to phospholipid bilayers. Biochemistry 42, 6333-6340.

Zeri, et al. (2003). Structure of the coat protein in fd filamentous bacteriophage particles determined by solid-state NMR spectroscopy. Proc Natl Acad Sci USA 100, 6458-6463.

Zheng et al. (2003). Automated protein fold determination using a minimal NMR constraint strategy. Protein Science 12, 1232-1246.

Zimmerman, et al. (1995). Automated analysis of nuclear magnetic resonance assignments for proteins. Curr Opin Struct Biol 5. 664-673.

Zimmerman, et al. (1997). Automated analysis of protein NMR assignments using methods from artificial intelligence. J Mol Biol 269, 592-610.

\* cited by examiner

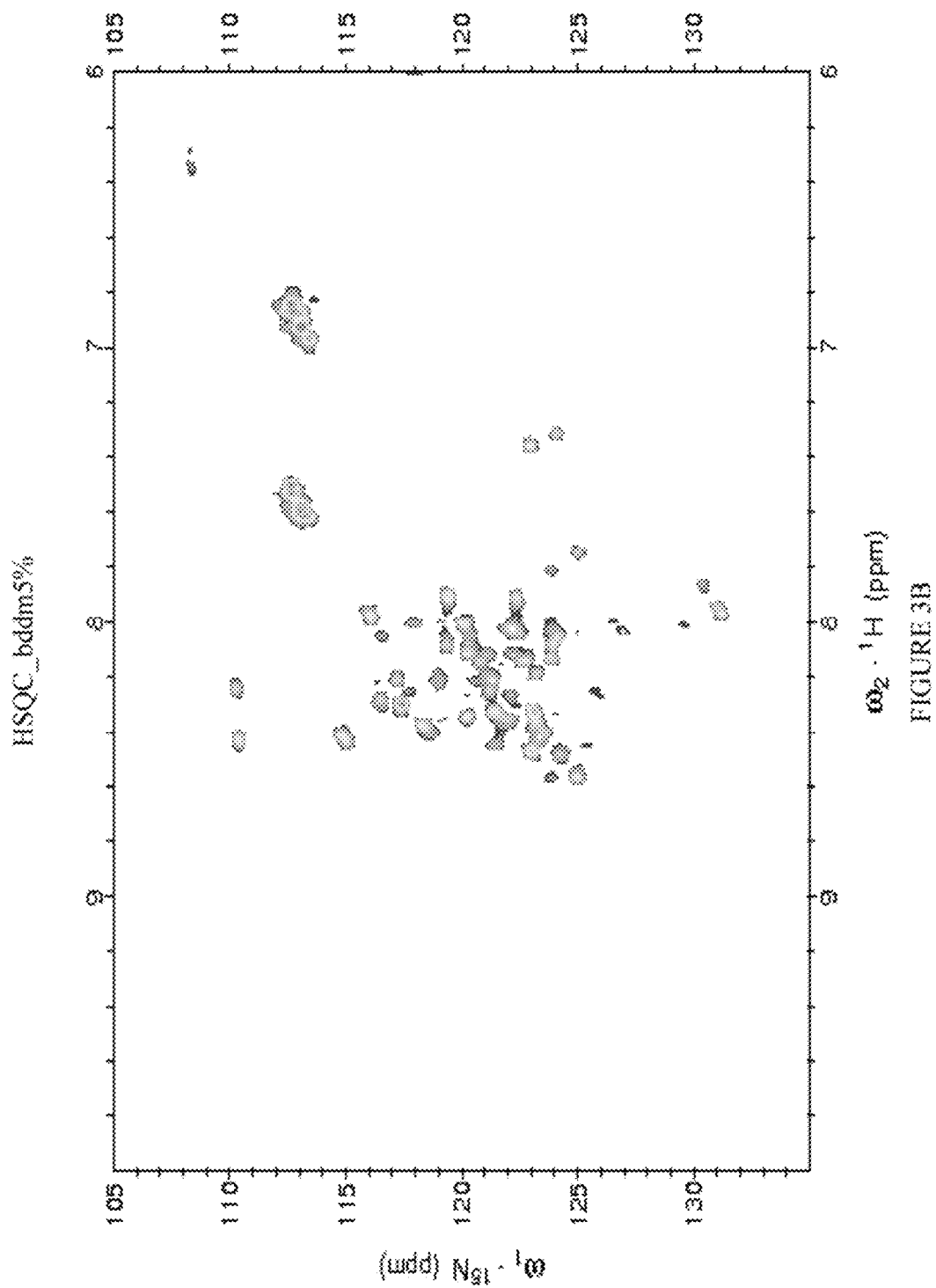

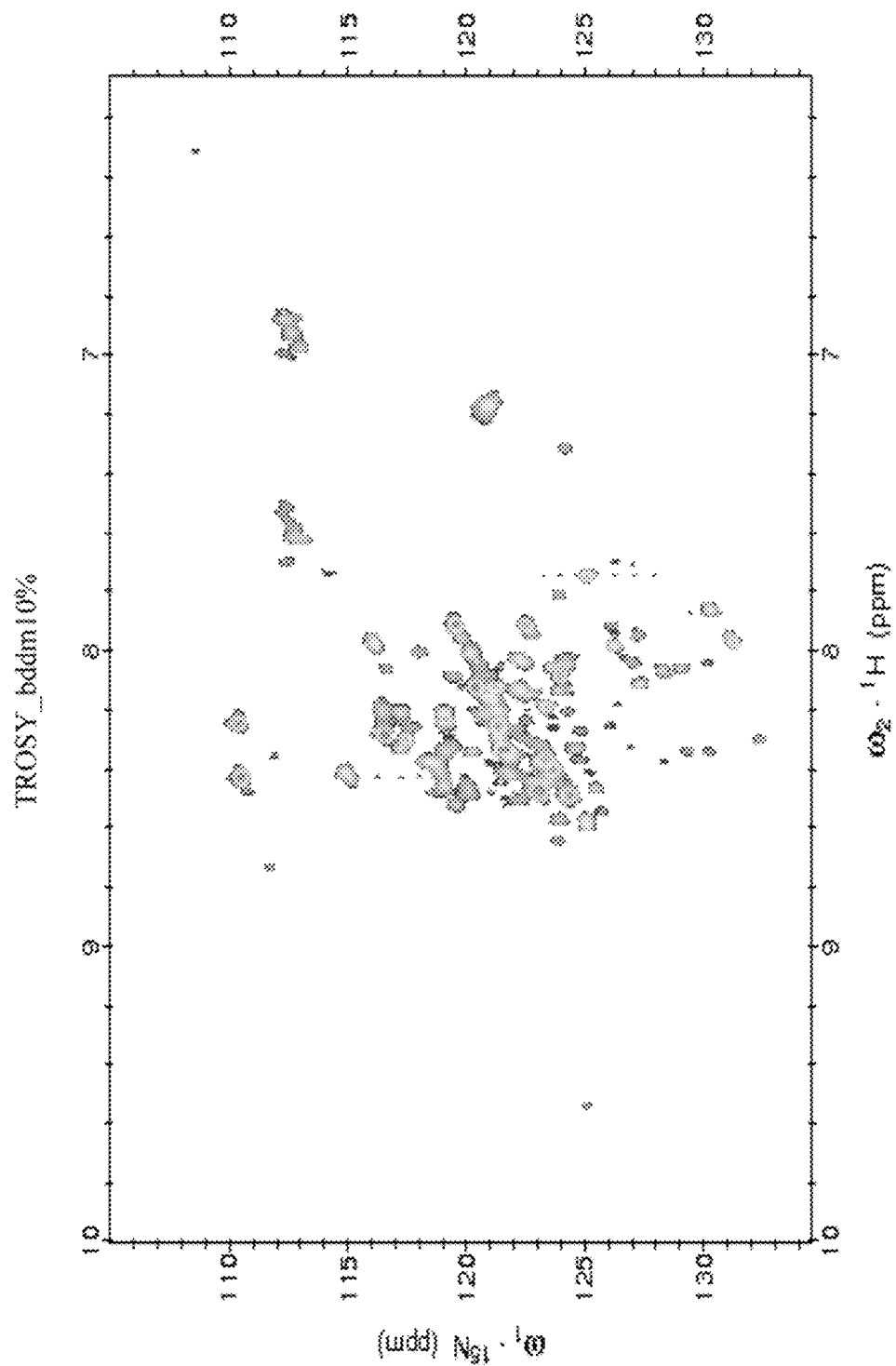

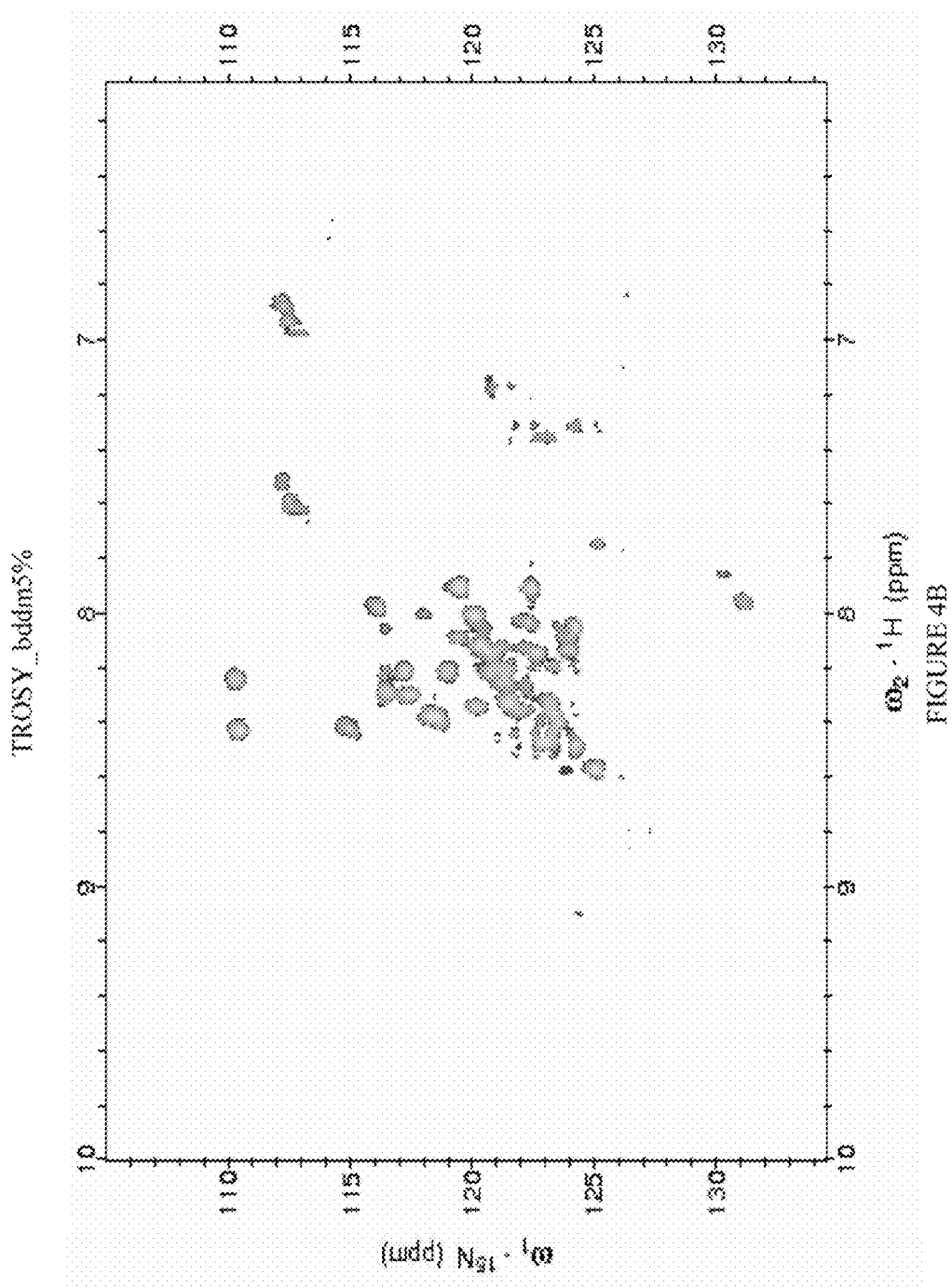

SEQUENCE LISTING

<160> NUMBER OF SEQ ID NOS: 1

<210> SEQ ID NO 1
<211> LENGTH: 81
<212> TYPE: PRT
<213> ORGANISM: Escherichia coli

<400> SEQUENCE: 1

```
Met Asn His Lys Val His His His His His Ile Glu Gly Arg His
1               5                   10                  15

Met Ala Val Gln Thr Pro Arg Gln Arg Leu Ala Asn Ala Lys Phe Asn
            20                  25                  30

Lys Asn Asn Glu Lys Tyr Arg Lys Tyr Gly Lys Lys Lys Glu Gly Lys
        35                  40                  45

Thr Glu Lys Thr Ala Pro Val Ile Ser Lys Thr Trp Leu Gly Ile Leu
    50                  55                  60
```

```
Leu Phe Leu Leu Val Gly Gly Gly Val Leu Gln Leu Ile Ser Tyr Ile
65                  70                  75                  80
Leu
```

LABELED BIOMOLECULAR COMPOSITIONS AND METHODS FOR THE PRODUCTION AND USES THEREOF

CLAIM OF PRIORITY

This application claims priority to U.S. Provisional Application No. 60/918,418, filed Mar. 16, 2007, the disclosure of which is hereby incorporated by reference in its entirety.

STATEMENT REGARDING FEDERALLY SPONSORED RESEARCH

This invention was made with government support under NIH Grant Numbers U54 GMO74958 and U54 GM075026.

STATEMENT REGARDING SEQUENCES AND REFERENCES

The sequence listing provided in the ASCII text file 18622-78SEQ.txt, 2 KB, created Jan. 17, 2013 is hereby incorporated by reference in its entirety. All patents, publications and non-patent references referred to herein shall be considered incorporated by reference into this application in their entireties.

BACKGROUND OF THE INVENTION

Determination of precise and accurate protein structures by Nuclear Magnetic Resonance (hereinafter "NMR") generally requires weeks or even months to acquire and interpret all of the necessary NMR data, particularly for completing side chain resonance assignments. However, medium-accuracy fold information can often provide important and helpful clues about protein evolution and biochemical function(s). A largely automatic strategy for rapid determination of medium-accuracy protein backbone structures has been previously described (Zheng, D., Huang, Y. J., Moseley, H. N. B., Xiao, R., Aramini, J., Swapna, G. V. T.; Montelione, G. T. (2003) *Automated protein fold determination using a minimal NMR constraint strategy*. Protein Science 2003, 12: 1232-1246.). This strategy of rapid fold determination derives from ideas originally introduced for determining medium-accuracy NMR structures of large proteins (Gardner, K. H., Rosen, M. K., and Kay, L. E. (1997). *Global folds of highly deuterated, methyl-protonated proteins by multidimensional NMR*. Biochemistry 36, 1389-1401.), using deuterated, $^{13}$C—, $^{15}$N-enriched protein samples with selective protonation of sidechain methyl groups ($^{13}$CH$_3$). Data collection includes acquiring NMR spectra suitable for automatic analysis of assignments for backbone and sidechain $^{15}$N, H$^N$ resonances, and sidechain $^{13}$CH$_3$ methyl resonances. In some cases, assignments are also determined for $^1$H and/or $^{13}$C atoms of labeled Tyr and Phe residues. NMR resonance assignments can be determined by automated NMR assignment programs, such as the program AutoAssign (Moseley, H. N., Monleon, D., and Montelione, G. T. (2001). *Automatic determination of protein backbone resonance assignments from triple resonance nuclear magnetic resonance data*. Methods Enzymol 339, 91-108; Moseley, H. N., and Montelione, G. T. (1999). *Automated analysis of NMR assignments and structures for proteins*. Curr Opin Struct Biol 9, 635-642; Zimmerman, D. E., Kulikowski, C. A., Huang, Y.; Feng, W., Tashiro, M., Shimotakahara, S., Chien, C., Powers, R., and Montelione, G. T. (1997). *Automated analysis of protein NMR assignments using methods from artificial intelligence*. J Mol Biol 269, 592-610; Zimmerman, D. E., and Montelione, G. T. (1995). *Automated analysis of nuclear magnetic resonance assignments for proteins*. Curr Opin Struct Biol 5, 664-673). Three-dimensional structures can be analyzed automatically with programs like AutoStructure (Huang, Y. J., Moseley, H. N., Baran, M. C., Arrowsmith, C., Powers, R., Tejero, R., Szyperski, T., and Montelione, G. T. (2005). *An integrated platform for automated analysis of protein NMR structures*. Methods Enzymol 394, 111-141; Huang, Y. J., Tejero, R., Powers, R., and Montelione, G. T. (2006). *A topology-constrained distance network algorithm for protein structure determination from NOESY data*. Proteins 62, 587-603). The total time required for collecting and processing NMR spectra for the medium-accuracy strategy can be relatively short. For example, using NMR data on $^2$H, $^{13}$C, $^{15}$N-enriched proteins with protonated methyl (and/or aromatic) groups, published NMR software packages like AutoAssign and AutoStructure can be used to process NMR spectra, carry out resonance assignments, interpret Nuclear Overhauser Enhancement Spectroscopy (hereinafter "NOESY") data, and generate medium-accuracy structures within a few days. These structures provide essential three-dimensional information for characterizing biological activities of proteins, and are good starting points for further refinement to high precision and accuracy using additional NMR data. The feasibility of this combined data collection and analysis strategy starting from raw NMR time domain data has already been demonstrated by automatic analysis of a medium accuracy structure of the Z domain of Staphylococcal protein A (Zheng, D., Huang, Y. J., Moseley, H. N. B., Xiao, R., Aramini, J., Swapna, G. V. T.; Montelione, G. T. (2003) *Automated protein fold determination using a minimal NMR constraint strategy*. Protein Science 2003, 12: 1232-1246).

Perdeuteration (the enrichment of proteins with $^2$H) is also a prerequisite for using some of the most advanced NMR methods for studying the three-dimensional structures of membrane proteins by NMR (Arora, A., Abildgaard, F., Bushweller, J. H., and Tamm, L. K. (2001). *Structure of outer membrane protein A transmembrane domain by NMR spectroscopy*. Nat Struct Biol 8, 334-338; Fernandez, C., Hilly, C., Wider, G., Guntert, P., and Wuthrich, K. (2004). *NMR structure of the integral membrane protein OmpX*. J Mol Biol 336, 1211-1221; Fernandez, C., Hilty, C., Wider, G., and Wuthrich, K. (2002). *Lipid-protein interactions in DHPC micelles containing the integral membrane protein OmpX investigated by NMR spectroscopy*. Proc Natl Acad Sci USA 99, 13533-13537; Fernandez, C., and Wuthrich, K. (2003). *NMR solution structure determination of membrane proteins reconstituted in detergent micelles*. FEBS Lett 555, 144-150; Sorgen, P. L., Cahill, S. M., Krueger-Koplin, R. D., Krueger-Koplin, S. T., Schenck, C. C., and Girvin, M. E. (2002a). *Structure of the Rhodobacter sphaeroides light-harvesting 1 beta subunit in detergent micelles*. Biochemistry 41, 31-41; Sorgen, P. L., Hu, Y., Guan, L., Kaback, H. R., and Girvin, M. E. (2002b). *An approach to membrane protein structure without crystals*. Proc Natl Acad Sci USA 99, 14037-14040; Tamm, L. K., Abildgaard, F., Arora, A., Blad, H., and Bushweller, J. H. (2003). *Structure, dynamics and function of the outer membrane protein A (OmpA) and influenza hemagglutinin fusion domain in detergent micelles by solution NMR*. FEBS Lett 555, 139-143)). These methods require use of $^2$H, $^{13}$C, $^{15}$N-enriched membrane protein samples with $^{13}$C—1H (or $^{12}$C—$^1$H) methyl labels. Production of such samples can be expensive ($1,500-$10,000 per sample), limiting the applicability of this approach. The high cost of sample production greatly limits the applicability of powerful automated structure analysis methods (Zheng, D., Huang, Y. J., Moseley, H. N. B., Xiao, R., Aramini, J., Swapna, G. V. T.; Montelione, G. T. (2003) *Automated protein fold determination using a minimal NMR constraint strategy*. Protein Science 2003, 12: 1232-1246.) and certain powerful membrane protein structure analysis methods (Arora, A., Abildgaard, F., Bushweller, J. H., and Tamm, L. K. (2001). *Structure of outer membrane protein A transmembrane domain by NMR spectroscopy*. Nat Struct Biol 8, 334-338; Fernandez, C., Hilty, C., Wider, G., Guntert, P., and Wuthrich, K. (2004). *NMR structure of the integral membrane protein OmpX*. J Mol Biol 336, 1211-1221; Fernandez, C., Hilty, C., Wider, G., and Wuthrich, K. (2002). *Lipid-protein interactions in DHPC micelles containing the integral membrane protein OmpX investigated by NMR spectroscopy*. Proc Natl Acad Sci USA 99, 13533-13537; Fernandez, C., and Wuthrich, K. (2003). *NMR solution structure determination of membrane proteins reconstituted in detergent micelles*. FEBS Lett 555, 144-150; Sorgen, P. L., Cahill, S. M., Krueger-Koplin, R. D., Krueger-Koplin, S. T., Schenck, C. C., and Girvin, M. E. (2002a). *Structure of the Rhodobacter sphaeroides light-harvesting 1 beta subunit in detergent micelles*. Biochemistry 41, 31-41; Sorgen, P. L., Hu, Y., Guan, L., Kaback, H. R., and Girvin, M. E. (2002b). *An approach to membrane protein structure without crystals*. Proc Natl Acad Sci USA 99, 14037-14040; Tamm, L. K., Abildgaard, F., Arora, A., Blad, H., and Bushweller, J. H. (2003). *Structure, dynamics and function of the outer membrane protein A (OmpA) and influenza hemagglutinin fusion domain in detergent micelles by solution NMR*. FEBS Lett 555, 139-143)).

There are three principle approaches for membrane protein structure analysis by NMR. The first approach is solution-state NMR, which can be used to determine three-dimensional structures of detergent-solubilized membrane proteins using conventional triple-resonance NMR methods with sensitivity-enhanced Transverse Relaxation Optimized Spectroscopy (hereinafter "TROSY") detection methods (Arora, A., Abildgaard, F.; Bushweller, J. H., and Tamm, L. K. (2001). *Structure of outer membrane protein A transmembrane domain by NMR spectroscopy*. Nat Struct Biol 8, 334-338; Fernandez, C., Hilty, C., Wider, G., Guntert, P., and Wuthrich, K. (2004). *NMR structure of the integral membrane protein OmpX*. J Mol Biol 336, 1211-1221; Fernandez, C., Hilty, C., Wider, G., and Wuthrich, K. (2002). *Lipid-protein interactions in DHPC micelles containing the integral membrane protein OmpX investigated by NMR spectroscopy*. Proc Natl Acad Sci USA 99, 13533-13537; Fernandez, C., and Wuthrich, K. (2003). *NMR solution structure determination of membrane proteins reconstituted in detergent micelles*. FEBS Left 555, 144-150; Sorgen, P. L., Cahill, S. M., Krueger-Koplin, R. D., Krueger-Koplin, S. T., Schenck, C. C., and Girvin, M. E. (2002a). *Structure of the Rhodobacter sphaeroides light-harvesting 1 beta subunit in detergent micelles*. Biochemistry 41, 31-41; Sorgen, P. L., Hu, Y., Guan, L., Kaback, H. R., and Girvin, M. E. (2002b). *An approach to membrane protein structure without crystals*. Proc Natl Acad Sci USA 99, 14037-14040; Tamm, L. K., Abildgaard, F., Arora, A., Blad, H., and Bushweller, J. H. (2003). *Structure, dynamics and function of the outer membrane protein A (OmpA) and influenza hemagglutinin fusion domain in detergent micelles by solution NMR*. FEBS Lett 555, 139-143). The methods under this approach require the use of $^2$H, $^{13}$C, $^{15}$N-enriched membrane protein samples with $^{13}$C—$^1$H methyl labels.

The other two approaches are two methods of solid-state NMR, which have been successfully applied to membrane protein structure analysis. One of these approaches, Oriented Solid-State NMR, uses molecular orientation to overcome the line-broadening effects of dipolar coupling and chemical shift that otherwise complicate solid-state NMR spectra of proteins. Pioneered for applications to membrane proteins, samples of lipid bilayers or bicelles are statically-oriented in a special NMR probe, providing a high resolution NMR spectrum that includes information about interatomic bond orientations. This approach, while still under development, has already been used to determine three-dimensional structures of small membrane proteins in lipid bilayers (De Angelis, A. A., Howell, S. C., Nevzorov, A. A., and Opella, S. J. (2006). *Structure determination of a membrane protein with two trans-membrane helices in aligned phospholipid bicelles by solid-state NMR spectroscopy*. J Am Chem Soc 128, 12256-12267; Kim; S., Quine, J. R., and Cross, T. A. (2001). *Complete cross-validation and R-factor calculation of a solid-state NMR derived structure*. J Am Chem Soc 123, 7292-7298; Marassi, F. M., and Opella, S. J. (2002). *Using pisa pies to resolve ambiguities in angular constraints from PISEMA spectra of aligned proteins*. J Biomol NMR 23, 239-242; Marassi, F. M., and Opella, S. J. (2003). *Simultaneous assignment and structure determination of a membrane protein from NMR orientational restraints*. Protein Sci 12, 403-411; Opella, S. J. (2003). *Membrane protein NMR studies*. Methods Mol Biol 227, 307-320; Park, S. H., Mrse, A. A., Nevzorov, A. A., Mesleh, M. F., Oblatt-Montal, M., Montal, M., and Opella, S. J. (2003). *Three-dimensional structure of the channel-forming trans-membrane domain of virus protein "u" (Vpu) from HIV-1*. J Mol Biol 333, 409-424; Valentine, K. G., Mesleh, M. F., Opella, S. J., Ikura, M., and Ames, J. B. (2003). *Structure, topology, and dynamics of myristoylated recoverin bound to phospholipid bilayers*. Biochemistry 42, 6333-6340; Zeri, A. C., Mesleh, M. F., Nevzorov, A. A., and Opella, S. J. (2003). *Structure of the coat protein in fd filamentous bacteriophage particles determined by solid-state NMR spectroscopy*. Proc Natl Acad Sci USA 100, 6458-6463).

The second solid-state NMR approach, Magic Angle Spinning (hereinafter "MAS") NMR, provides another method for narrowing the broad lines of solid-state NMR samples by minimizing the effects of dipolar coupling by rapidly spinning the solid sample at a special orientation (54.7°) relative to the applied magnetic field. MAS methods have been further developed to the point where it is now possible to obtain complete resonance assignments and three-dimensional structures of small proteins in the solid state, including membrane proteins (Astrof, N. S., Lyon, C. E., and Griffin, R. G. (2001). *Triple resonance solid state NMR experiments with reduced dimensionality evolution periods*. J Magn Reson 152, 303-307; Castellani, F., van Rossum, B., Diehl, A., Schubert, M., Rehbein, K., and Oschkinat, H. (2002). *Structure of a protein determined by solid-state magicangle-spinning NMR spectroscopy*. Nature 420, 98-102; Castellani, F., van Rossum, B. J., Diehl, A., Rehbein, K., and Oschkinat, H. (2003). *Determination of solid-state NMR structures of proteins by means of three-dimensional 15N-13C-13C dipolar correlation spectroscopy and chemical shift analysis*. Biochemistry 42, 11476-11483; Igumenova, T. I., McDermott, A. E. Zilm, K. W., Martin, R. W., Paulson, E. K., and Wand, A. J. (2004a). *Assignments of carbon NMR resonances for microcrystalline ubiquitin*. J Am Chem Soc 126, 6720-6727; Igumenova, T. I., Wand, A. J., and McDermott, A. E. (2004b). *Assignment of the backbone resonances for microcrystalline ubiquitin*. J Am Chem Soc 126, 5323-5331; Jaroniec, C. P., MacPhee, C. E., Bajaj, V. S., McMahon, M. T., Dobson, C. M., and Griffin, R. G. (2004). *High-resolution molecular structure of a peptide in an amyloid fibril determined by magic angle spinning NMR spectroscopy*. Proc Natl Acad Sci USA 101, 711-716; Krabben, L., van Rossum, B. J., Castellani, F., Bocharov, E., Schulga, A. A., Arseniev, A. S., Weise, C., Hucho, F., and Oschkinat, H. (2004). *Towards structure determination of neurotoxin II bound to nicotinic acetylcholine receptor: a solid-state NMR approach*. FEBS Lett 564, 319-324; Petkova, A. T., Baldus, M., Belenky, M., Hong, M., Griffin, R. G., and Herzfeld, J. (2003). *Backbone and side chain assignment strategies for multiply labeled membrane peptides and proteins in the solid state*. J Magn Reson 160, 1-12; Rienstra, C. M., Tucker-Kellogg, L., Jaroniec, C. P., Hohwy, M., Reif, B., McMahon, M. T., Tidor, B., Lozano-Perez, T., and Griffin, R. G. (2002). *De novo determination of peptide structure with solid-state magic-angle spinning NMR spectroscopy*. Proc Natl Acad Sci USA 99, 10260-10265).

Solid-state NMR has tremendous potential for providing three-dimensional structures of many membrane proteins that cannot be crystallized. Oriented Solid-State NMR experiments are particularly well-suited for determining structures of helical membrane proteins, and MAS experiments, which can identify dipolar interactions between backbone atoms in adjacent beta strands, are especially well-suited for beta-type membrane structures, though it may also be possible to determine structures of alpha-helical proteins with these new methods.

NMR has special value in structural genomics efforts for rapidly characterizing the "foldedness" of specific protein constructs (Kennedy, M. A., Montelione, G. T, Arrowsmith, C. H., and Markley, J. L. (2002). *Role for NMR in structural genomics*. J Struct Funct Genomics 2, 155-169; Montelione, G. T (2001). Structural genomics: an approach to the protein folding problem. Proc Natl Acad Sci USA 98, 13488-13489). The dispersion and line shapes of resonances measured in one-dimensional $^1$H-NMR and two dimensional $^{15}$N—$^1$H or $^{13}$C—$^1$H correlation spectra provide "foldedness" criteria with which to define constructs and solution conditions that provide folded protein samples (see FIG. 1). The required isotopic enrichment with $^{15}$N is relatively inexpensive, and the two-dimensional $^{15}$N—$^1$H correlation spectra can be recorded in tens of minutes with conventional NMR systems.

An *E. coli* Single Protein Production (hereinafter "SPP") bacterial expression system has been previously described that utilizes a combination of attributes—cold-inducible promoters, low temperature, induction of the mRNA-specific endoribonuclease MazF causing host cell growth arrest, and culture condensation—to facilitate stable, high level protein expression (almost 30% of total cellular protein) without background protein synthesis (Suzuki, M., Roy, R., Zheng, H., Woychik, N., and Inouye, M. (2006). *Bacterial bioreactors for high yield production of recombinant protein*. J Biol Chem 281, 37559-37565; Suzuki, M., Zhang, J., Liu, M., Woychik, N. A., and Inouye, M. (2005). *Single protein production in living cells facilitated by an mRNA interferase*. Mol Cell 18, 253-261). This expression system has been shown to provide specific labeling with selenomethionine and fluorophenylalanine (Suzuki, M., Roy, R., Zheng, H., Woychik, N., and Inouye, M. (2006). *Bacterial bioreactors for high yield production of recombinant protein*. J Biol Chem 281, 37559-37565). Moreover, using an optimized SPP vector, exponentially growing cultures can be condensed 40-fold without significantly affecting protein yields (Suzuki, M., Roy, R., Zheng, H., Woychik, N., and Inouye, M. (2006). *Bacterial bioreactors for high yield production of recombinant protein*. J Biol Chem 281, 37559-37565). This has the potential to lower sample labeling costs to a small percentage of the cost of traditional isotope-labeling experiments.

The compositions, systems, and methods of the present invention provide effective means to screen conditions for membrane protein purification, membrane protein structure analysis, and to determine three-dimensional protein structures using deuterium-decoupled NMR methods suitable for rapid structure analysis and analysis of large protein structures. The present invention is also advantageous in that it provides means for production of deuterated protein samples at reduced cost.

SUMMARY OF THE INVENTION

Disclosed herein are novel processes for (i) producing $^2$H, $^{13}$C, $^{15}$N enriched proteins using an *E. coli* SPP-NMR expression system (as further described herein), (ii) using isotope-enriched membrane proteins produced with an SPP-NMR system for screening detergent conditions suitable for purification and/or three-dimensional structure analysis, and (iii) labeling with $^{13}$C—$^{15}$N specific peptide bonds in proteins (further described and referred to herein as SPP-PBL). The methods of isotope-enrichment can be combined with high throughput data collection and analysis methods to provide rapid analysis of small protein structures by NMR. Conditions identified by detergent screening can be used for purifying membrane proteins or for direct determination of their three-dimensional structures by NMR without purification.

In certain embodiments, the present invention is directed to compositions, systems, and methods for producing $^2$H, $^{13}$C, $^{15}$N enriched proteins using an SPP-NMR system, methods for using these isotope-enriched proteins for screening detergent conditions suitable for purification and/or three-dimensional structure analysis, and labeling with $^{13}$C—$^{15}$N specific peptide bonds in proteins.

In other embodiments, the present invention is directed to an SPP-NMR system capable of separately inducing an mRNA-specific endoribonuclease and a target protein.

In further embodiments, the present invention is directed to a method of inducing a target protein by first contacting a vector containing a gene encoding an mRNA-specific endoribonuclease and a gene encoding a target protein with a composition suitable for inducing the mRNA-specific endoribonuclease, and then contacting the same vector with a composition suitable for inducing the target protein.

In other embodiments, the present invention is directed to a method of inducing a target protein by first contacting a vector containing a gene encoding an mRNA-specific endoribonuclease and a gene encoding a target protein with tetracycline to induce the mRNA-specific endoribonuclease, then eliminating background protein, then contacting the vector with an isotope-enriched media for a sufficient time to acclimate the vector to the media, and finally contacting the vector with IPTG to induce the target protein.

In further embodiments, the present invention is directed to a method of producing an isotope-labeled protein by first contacting a vector containing a gene encoding an mRNA-specific endoribonuclease and a gene encoding a target protein with a composition suitable to induce the mRNA-specific endoribonuclease, then contacting the vector with a selected isotope-labeled media to label the target protein, and finally contacting the vector with a composition suitable for inducing the target protein to produce an isotope-labeled protein.

In other embodiments, the present invention is directed toward a novel vector that contains the promoter-operator region of the tetA (tetA$^{PO}$) and tetR genes from Tn10 and a Multiple Cloning Site downstream of the tetA$^{PO}$, allowing two proteins to be induced independently.

BRIEF DESCRIPTION OF THE DRAWINGS

FIGS. 3A-E depict $^{15}$N—$^{1}$H HSQC spectra measured with non-purified, $^{15}$N-labeled RAMP-4 in (A) 10% (vol/vol) bddm (B) 5% (vol/vol) bddm (C) 10% (vol/vol) ldao (D) 10% (vol/vol) zwittergent and (E) 10% DPC (vol/vol) micelles.

FIGS. 4A-E depict $^{15}$N—$^{1}$H TROSY spectra of non-purified, $^{15}$N-labeled RAMP-4 in (A) 10% (vol/vol) bddm (B) 5% (vol/vol) bddm (C) 10% (vol/vol) ldao (D) 10% (vol/vol) zwittergent and (E) 10% DPC (vol/vol) micelles.

DETAILED DESCRIPTION OF THE INVENTION

Figure 1:
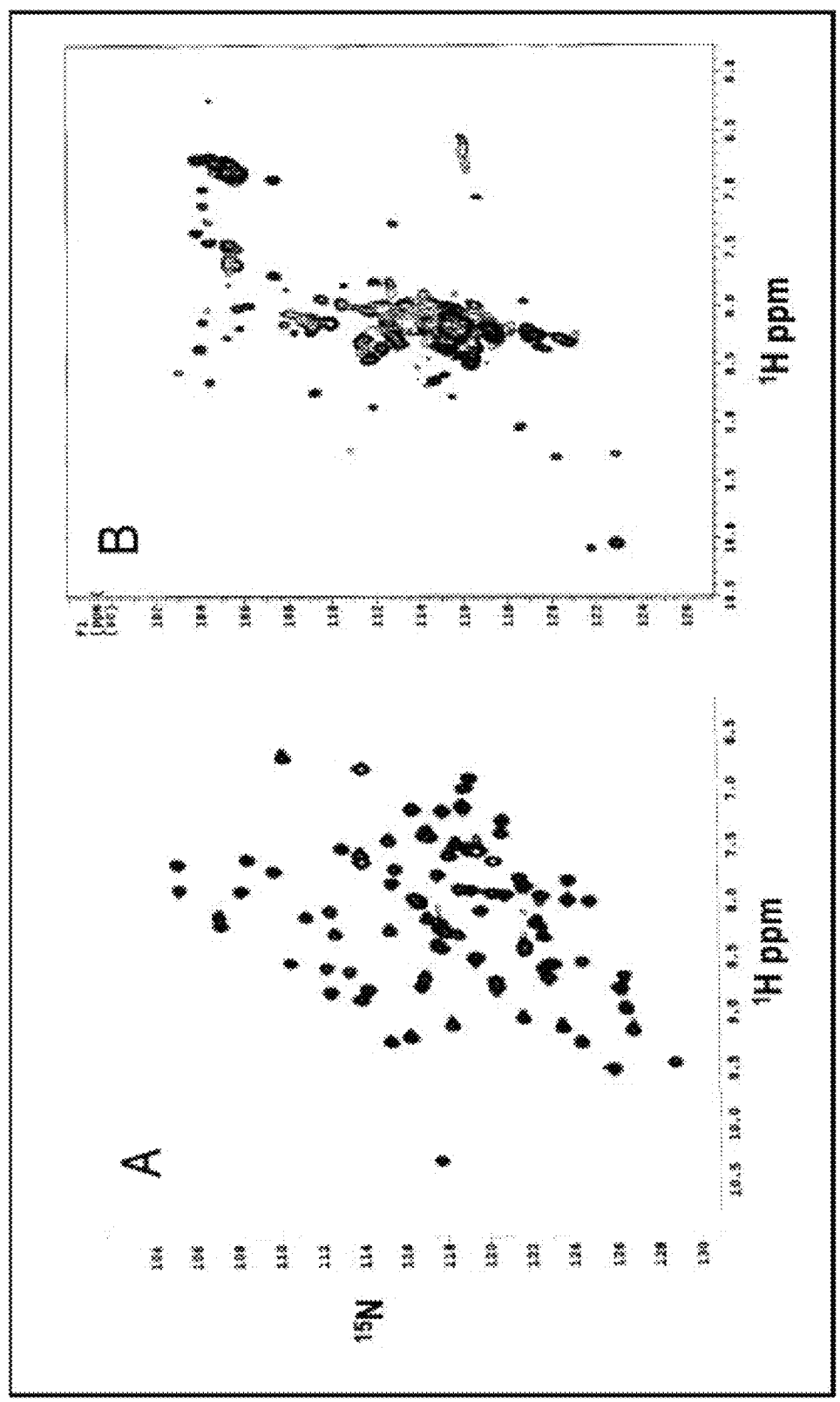
FIG. 1 depicts a comparison of $^{15}$N—$^1$H HSQC correlation spectra for disordered and well-folded proteins. (A) HSQC spectrum of T. thermophilus BRCT domain of the DNA ligase, a homologue of NESG target WR64, which has a well-defined three-dimensional structure in aqueous solution. (B) HSQC spectrum of D. melanogaster Par 1 C-terminal domain, a domain construct, which is predominantly disordered under the conditions of these measurements.

The claimed invention introduces a new technology that makes the SPP system more suitable for isotope-enrichment and perdeuteration of proteins. The claimed Single Protein Production-Nuclear Magnetic Resonance (hereinafter "SPP-NMR") system utilizes a cloned promoter-operator region of the tetA (tetA$^{PO}$) and tetR genes from Tn10. It is known that the expression of the tetA gene is repressed by TetR (tet repressor) and is regulated by tetracycline. Since the Multiple Cloning Site (hereinafter "MCS") exists downstream of tetA$^{PO}$, any gene of interest can be cloned into this plasmid. Therefore, expression of the gene cloned into the MCS is induced by the addition of tetracycline. The unique feature of the SPP-NMR system is that the mRNA-specific endoribonuclease and the target protein can be induced independently. In one embodiment of the claimed SPP-NMR system, the mazF gene is cloned into this tetracycline inducible vector, so that MazF and the target protein are induced by the addition of tetracycline and IPTG, respectively. However one skilled in the art would recognize that any mRNA-specific endoribonuclease gene could be substituted for the mazF gene in this embodiment. In contrast to the previous co-inducible system, the use of the new vector allows one to induce MazF or any other mRNA-specific endoribonuclease first, eliminate the background protein production, appropriately acclimate the cells in isotope-enriched media, and then induce the target protein. In this manner, one can now induce the production of the target protein only after the medium is exchanged with a specific medium for isotope labeling. This is an important new innovation that is essential for the practical production of perdeuterated membrane protein samples for NMR studies.

Protein Perdeuteration Using the SPP-NMR System

The high cost of obtaining $^{2}$H, $^{13}$C, $^{15}$N-enriched protein samples with $^{1}$H—$^{13}$C and/or $^{1}$H—$^{12}$C labeled methyls and/or aromatic sidechains remains a major bottleneck in the application of various NMR methods. The SPP-NMR System, which combines the SPP expression system with isotope labeling protocols, provides a powerful method to obtain NMR quality samples at a drastically reduced cost. A unique feature of the SPP-NMR System is the ability to not only grow cells in the absence of deuterium, but to condense bacteria cultures up to forty fold (40×) prior to the introduction of deuterium, isotope enriched media (Suzuki, M., Roy, R., Zheng, H., Woychik, N., and Inouye, M. (2006). *Bacterial bioreactors for high yield production of recombinant protein*. J Biol Chem 281, 37559-37565). This application can be applied to a variety of induction systems, including tetracycline and IPTG inducible systems. Condensation limits may vary depending on the protein of interest and therefore optimal fold-condensation needs to be evaluated individually for each protein target. Cultures are condensed on a small scale at 5×, 10×, 20×, 30×, and 40× and compared to 1× cultures. The highest fold condensation showing equal protein expression levels as 1× control is then chosen as optimal for labeling experiments.

The SPP-NMR method allows for soluble bacterial cell lysates to be analyzed directly or with minimal purification steps. Such analysis is possible since the only protein expressed, and therefore the only protein labeled following introduction of NMR isotopes, is the target protein. Once resuspended in a reduced volume, the protein of interest is expressed in a condensed state with no loss in overall yield. This results in a 5× to 40× cost reduction directly translating into a sample preparation cost reduction from $1500-$10,000 for traditional methods to $37.5-$250 when condensed 40× with the SPP-NMR method. The use of this technique is widely applicable to NMR spectroscopy allowing for the production of highly labeled samples suitable for obtaining rapid resonance assignments at a fraction of the cost.

When utilizing the SPP-NMR method for $^{2}$H labeling, cells are initially grown to an OD$_{600}$ between 0.5 and 0.6 in a defined minimal media such as M9-glucose or MJ9-glucose media (Jansson, M., Li, Y. C., Jendeberg, L., Anderson, S., Montelione, B. T., and Nilsson, B. (1996). *High-level production of uniformly $^{15}$N-and $^{13}$C-enriched fusion proteins in Escherichia coli*. J Biomol NMR 7, 131-141). This differs from traditional $^{2}$H labeling methods where cells must first grow in the presence of deuterium media to the proper cell density. Various acclimation steps that gradually increase the percent deuterium in the media are often necessary in order to allow cells to reach an OD$_{600}$ of 0.6 in fully deuterated minimal media. With the SPP-NMR method, once cells grown in H$_2$O media at 37° C. reach the proper density, they are then shifted to lower temperature (e.g. 15° C. shaker for 45 minutes) to acclimate the culture to cold shock conditions. Cold shock conditions facilitate a reduction in host cellular protein expression, a requirement for single protein production and culture condensation. Both the endoribonuclease MazF as well as the target protein are under the control of an inducible cold shock promoter. Expression of MazF is then induced with either tetracycline or IPTG for several hours (e.g., 16 hours and 3 hours respectively). In a preferred embodiment, following tetracycline-induced MazF expression and the onset of the resulting semi-quiescent state, cell cultures are centrifuged and rinsed in deuterated minimal media to remove residual H$_2$O, and finally resuspended in up to a 40× reduced volume of deuterium media containing $^{13}$C-deuterated glucose and $^{15}$N. Specific amino acid precursors (e.g. $^{13}$C-a-ketobutyric acid, $^{13}$C-a-ketoisovaleric acid, $^{1}$H—$^{13}$C—$^{15}$N-phenylalanine, and $^{1}$H—$^{13}$C—$^{15}$N-tyrosine) are then added to allow for selective $^{1}$H—$^{13}$C and/or $^{1}$H—$^{12}$C labeling of methyls and/or aromatic sidechains. Next, cultures are typically equilibrated in the absence of tetracycline or IPTG in the isotope enriched media for 1 hour (MazF$^{IPTG}$) or 4 hours (MazF$^{tet}$) (other times may be optimal for other specific systems) to allow for isotopes to permeate the cell prior to IPTG induction of the target protein. Finally, IPTG is added to the condensed cell cultures, inducing the production of the single target protein in deuterated, isotope containing media. Target protein production is allowed to proceed to a previously determined optimal expression time, typically 20 hours. At this point cultures are harvested by centrifugation, lysed, and soluble cell extracts are either analyzed directly or subsequent purification steps are carried out.

Figure 2:
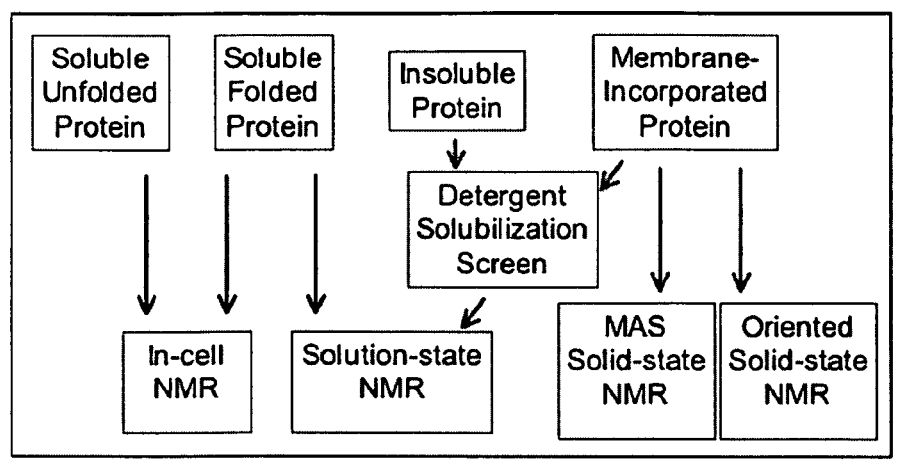
FIG. 2 depicts NMR methods for protein structure analysis without purification of isotope-enriched proteins produced with the SPP system.
Figure 3A:
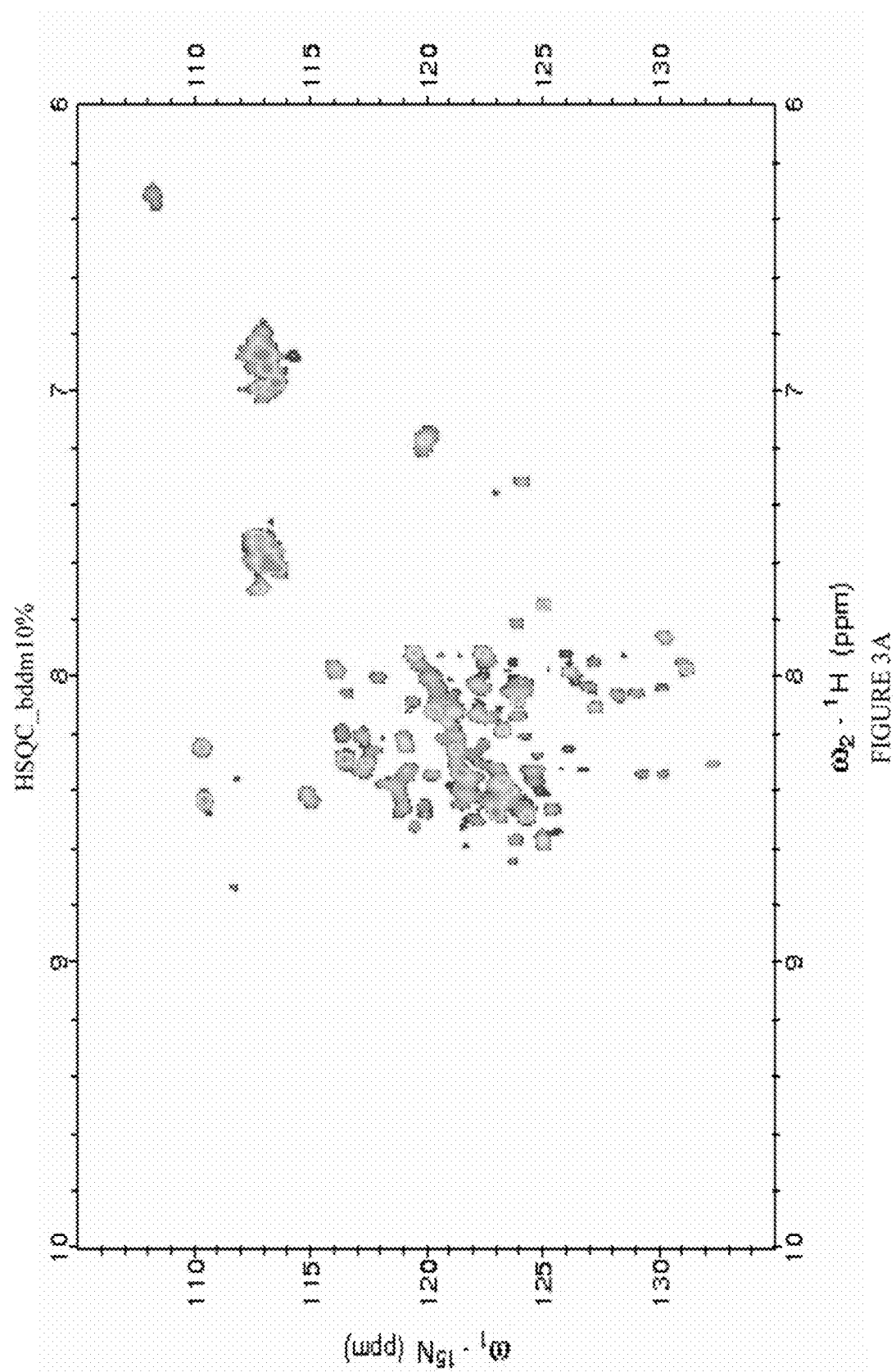
Figure 3C:
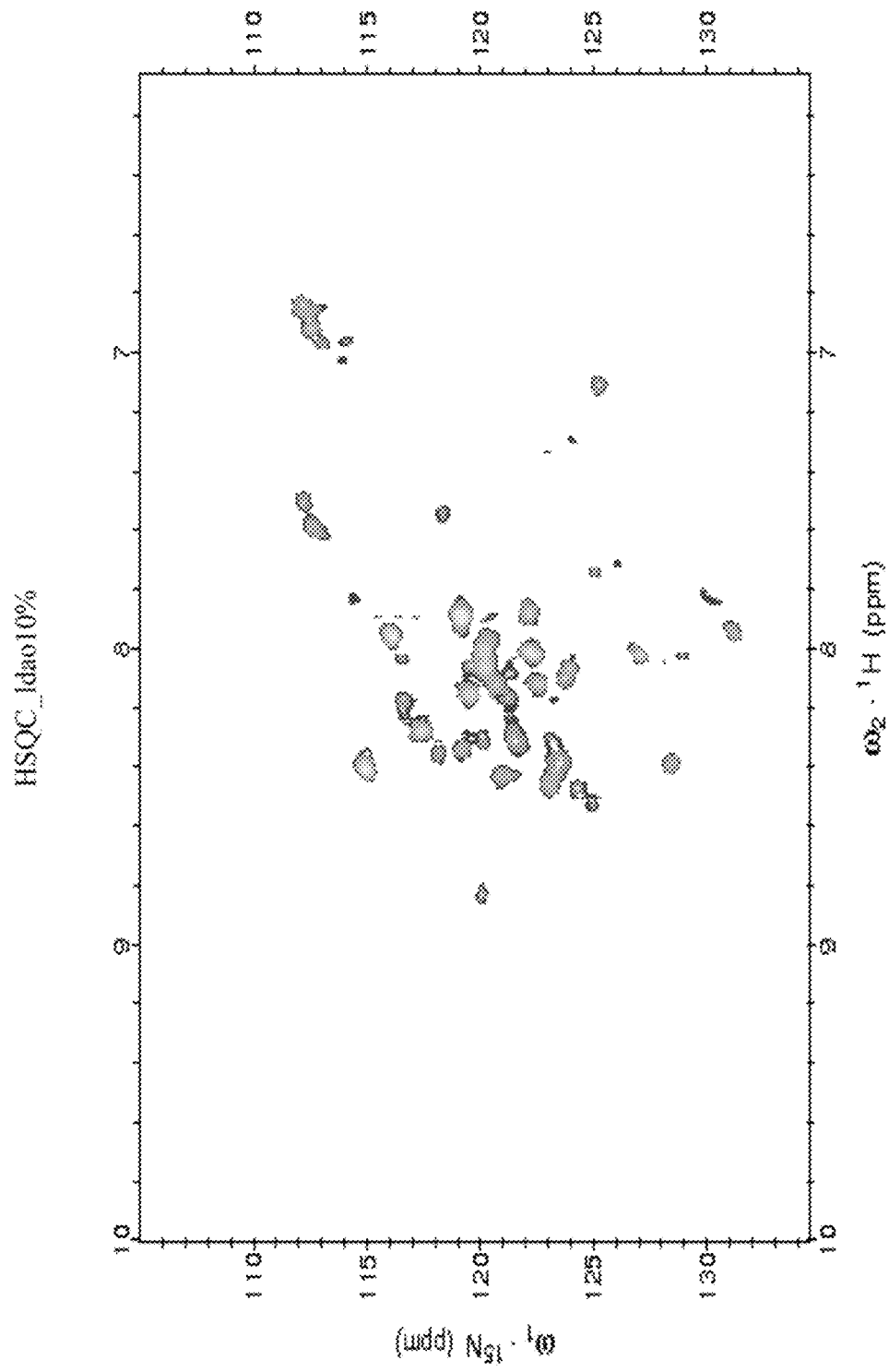
Figure 3D:
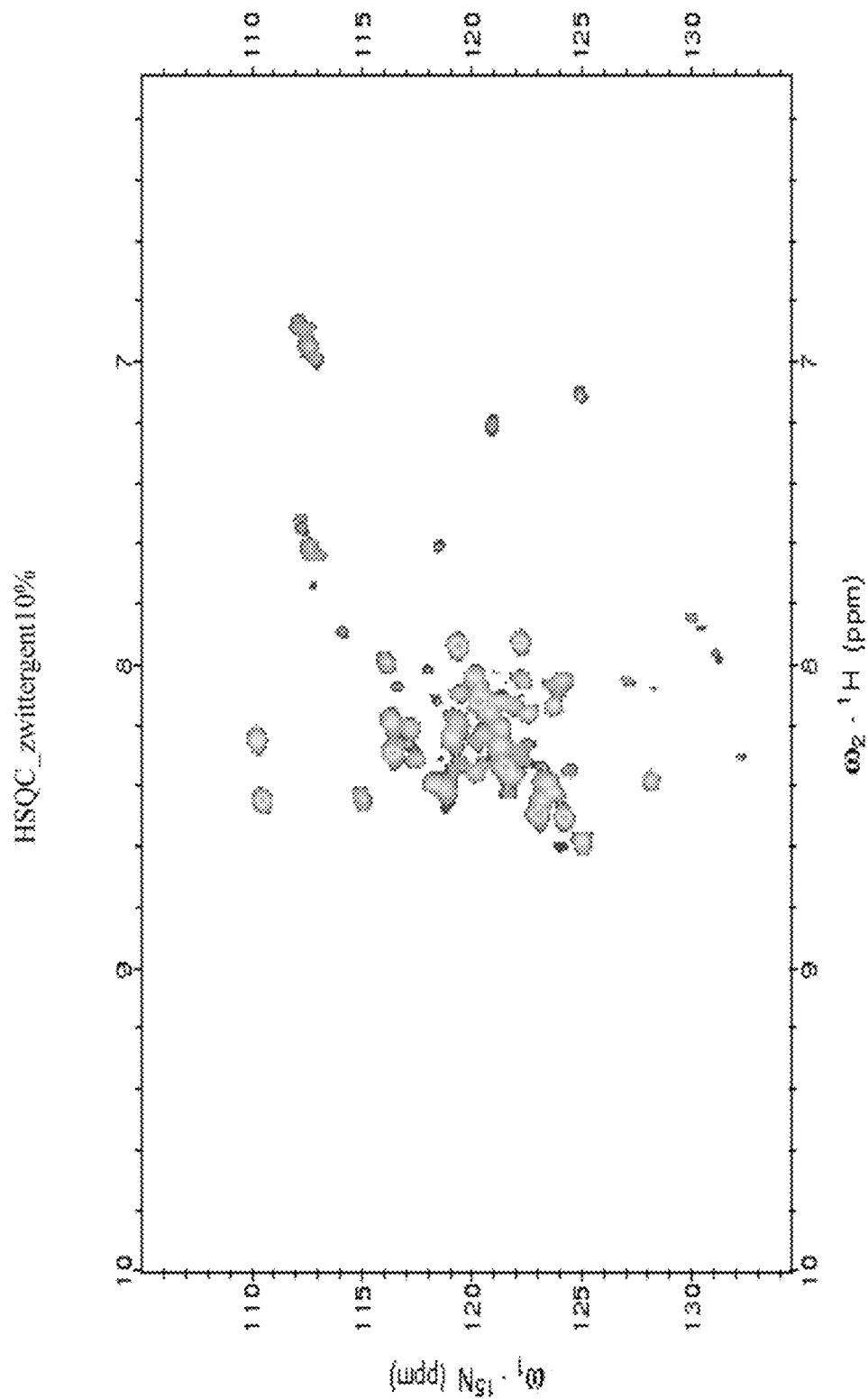
Figure 3E:
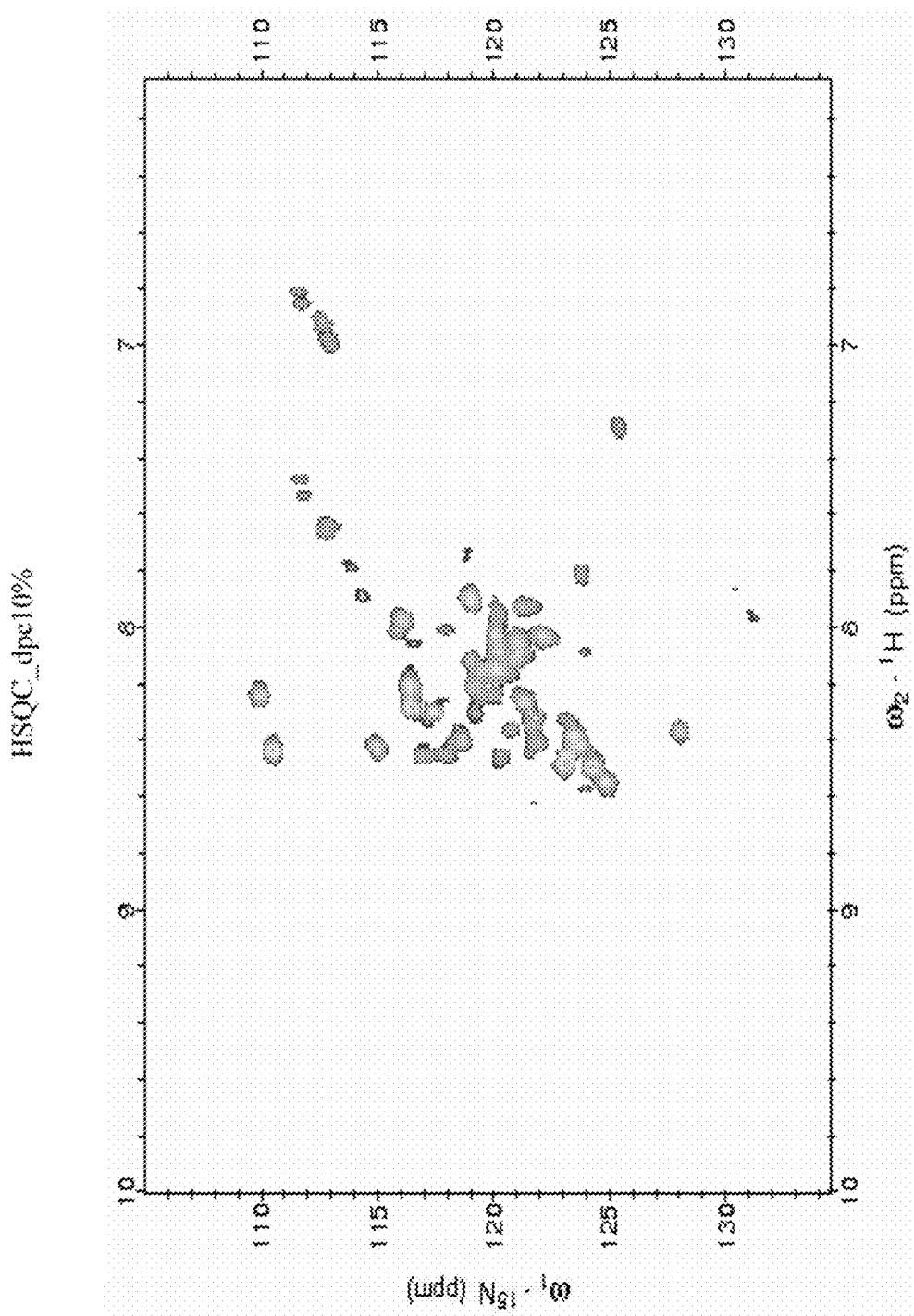

Using the SPP-NMR System to Prepare Membrane Proteins For Structure Analysis By NMR FIG. 2 outlines the four possible outcomes of a recombinant membrane protein expression experiment. If the protein is expressed in a recombinant host, it may generally be classified as soluble (or partially soluble) or insoluble (Acton, T. B., Gunsalus, K. C., Xiao, R., Ma, L. C., Aramini, J., Baran, M. C., Chiang, Y. W., Climent, T., Cooper, B., Denissova, N. G., et al. (2005). *Robotic cloning and Protein Production Platform of the Northeast Structural Genomics Consortium*. Methods Enzymol 394, 210-243). Soluble proteins can be further classified generally as "folded" or "unfolded" by using solution NMR, circular dichroism, or other methods. Most membrane proteins are "insoluble" in these simple assays; some because they are incorporated directly into membranes and others because they form inclusion bodies or other insoluble aggregates in the cell. The SPP-NMR System provides means for preparing isotope-enriched samples of these insoluble membrane proteins for structural analysis by solution state and solid state NMR.

Sample Preparation for Solution-State NMR Studies

Insoluble proteins, including those incorporated into membrane fractions and those that form inclusion bodies or are insoluble for other reasons, may be subjected to detergent screening methods in an attempt to solubilize them for solution-state NMR studies. An array of about 12-15 micelle- and bicelle-forming detergents has been developed for this "membrane protein detergent solubilization screen" (Krueger-Koplin, R. D., Sorgen, P. L., Krueger-Koplin, S. T., Rivera-Torres, I. O., Cahill, S. M., Hicks, D. B., Grinius, L., Krulwich, T. A., and Girvin, M. E. (2004). *An evaluation of detergents for NMR structural studies of membrane proteins*. J Biomol NMR 28, 43-57). The solubilization screen will provide a mixture of many micelle- or bicelle-solubilized proteins, of which only the target protein is isotopically-labeled, and circumvents the necessity to purify the target proteins. Detergent-solubilization will be evaluated initially using SDS-PAGE, and then using $^{15}$N—$^{1}$H Heteronuclear Single Quantum Coherence (hereinafter "HSQC"), $^{15}$N—$^{1}$H TROSY-HSQC, or similar kinds of NMR spectroscopy.

Robotic cloning protocols such as those described in Acton et al., 2005 (Acton, T. B., Gunsalus, K. C., Xiao, R., Ma, L. C., Aramini, J., Baran, M. C., Chiang, Y. W., Climent, T., Cooper, B. Denissova, N. G., et al. (2005). *Robotic cloning and Protein Production Platform of the Northeast Structural Genomics Consortium*. Methods Enzymol 394, 210-243), can be applied with the SPP-NMR labeling of membrane proteins to provide a high-throughput membrane protein solubilization screen. As encountered in developing robotic methods for crystallization-screening, some technical challenges in reproducible pipetting of viscous detergent solutions may be encountered. But the extensive experience in robotic Crystallization Technology Development by structural genomics groups will be valuable in future efforts to address these issues.

Detergent solubilized proteins that provide good quality HSQC spectra will then be prepared with $^{15}$N, $^{13}$C, and/or $^{2}$H enrichment, as appropriate to the size of the mixed-micelle or -bicelle system, using the SPP-NMR system for selective isotope enrichment. Resonance assignments and three-dimensional structures will then be pursued with standard TROSY-based triple-resonance NMR methods, typically using a high field (e.g. 800 MHz) NMR system with cryoprobe. As only the targeted protein is isotope-enriched, it should be quite feasible to carry out resonance assignments and complete three dimensional structure determinations of some membrane proteins by isotope-filtered solution NMR methods without the need for purifying the target protein.

Although it is possible to crystallize detergent-solubilized proteins, in these mixed-micelles the solubilized protein mixture is highly heterogeneous and not suitable for crystallization. However, the detergent conditions screened in this way provide guidance for which detergents can be used for purifying the membrane protein. This information can be used to purify target proteins for crystallization, or to purify isotope-enriched target proteins for NMR studies.

Sample Preparation For Solid-State NMR Studies

Targeted $^{15}$N-enriched proteins incorporated into membrane fractions, and without further purification, may be prepared in tens of milligram quantities and used for MAS and Oriented solid-state NMR analysis. These solid state NMR spectra will be used like solution-state NMR HSQC spectra to screen for membrane protein samples that provide good quality NMR data. If these samples provide good quality solid-state NMR spectra, additional protein samples with $^{15}$N, $^{13}$C, and/or $^{2}$H isotope enrichment should be provided to support efforts to carry out resonance assignments and three dimensional structures by solid state NMR (Drechsler, A., and Separovic, F. (2003). *Solid-state NMR structure determination*. IUBMB Life 55, 515-523).

Membrane proteins will be cloned and expressed in the SPP-NMR system, and then screened for soluble vs. insoluble behavior in whole cell extracts, using SDSPAGE gels to determine the fraction of expressed protein in the whole cell, soluble extract, and membrane-only fractions. In this way, each construct will be classified as "Soluble", "Insoluble/Membrane Associated", "Insoluble/Not-Membrane Associated". The rare soluble membrane protein samples will then be analyzed by HSQC screening of the whole cell extract. Insoluble protein constructs can be analyzed by two parallel pathways (illustrated in FIG. 2), utilizing either solid-state NMR methods or solution-state NMR methods.

Detergent Screening of Membrane Proteins That Have Been Isotope-Enriched with SPP System The use of the SPP-NMR system for selective isotope-enrichment and detergent screening of the ribosome-associated membrane protein 4 (RAMP-4) has been demonstrated. The protein sequence is (affinity purification tag italicized):

```
                                        (SEQ ID NO: 1)
MNHKVHHHHHHIEGRHMAVQTPRQRLANAKFNKNNEKYRKY

GKKKEGKTEKTAPVISKTWLGILLFLLVGOOVLQLISYIL
```

Figure 4C:
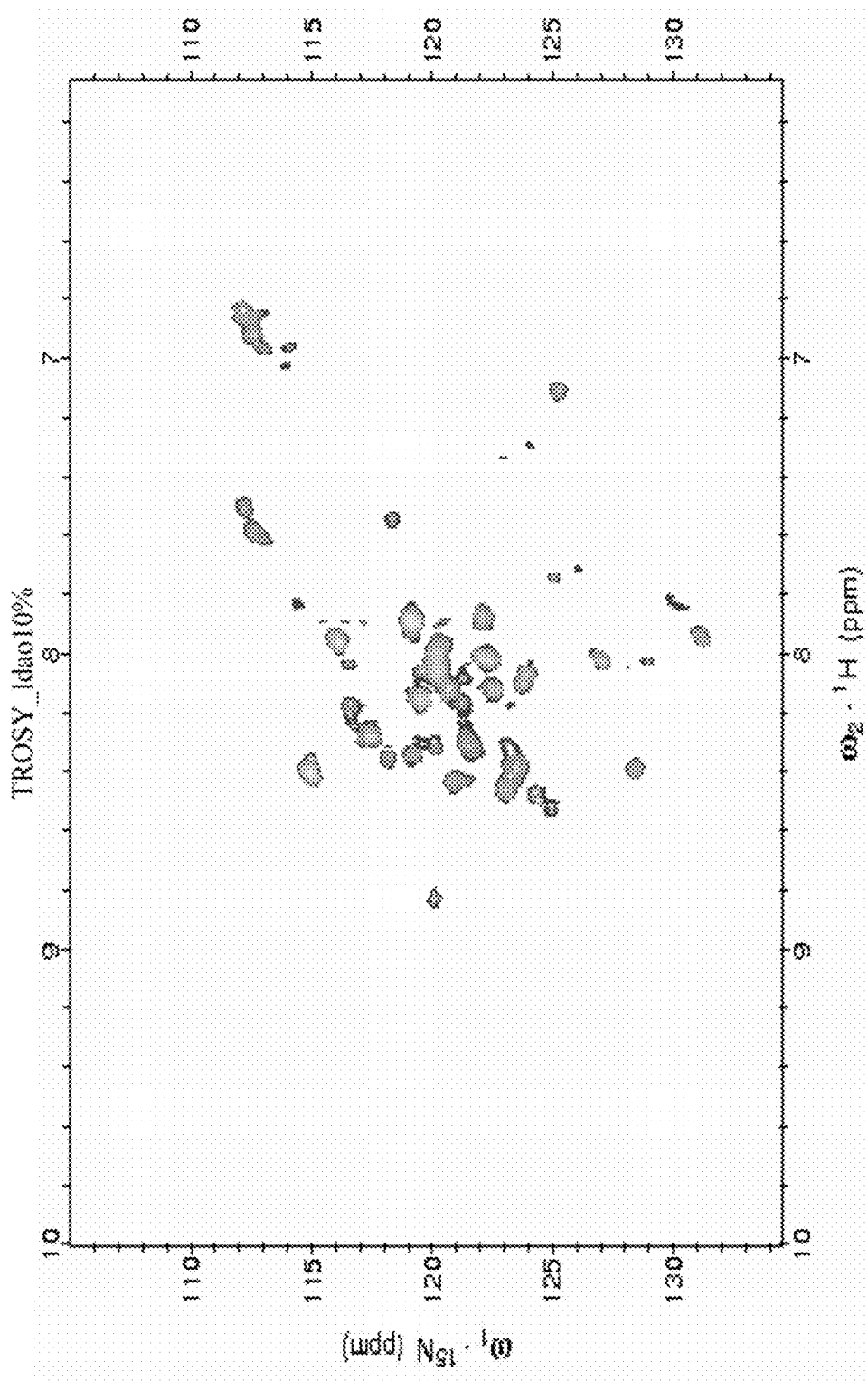
Figure 4D:
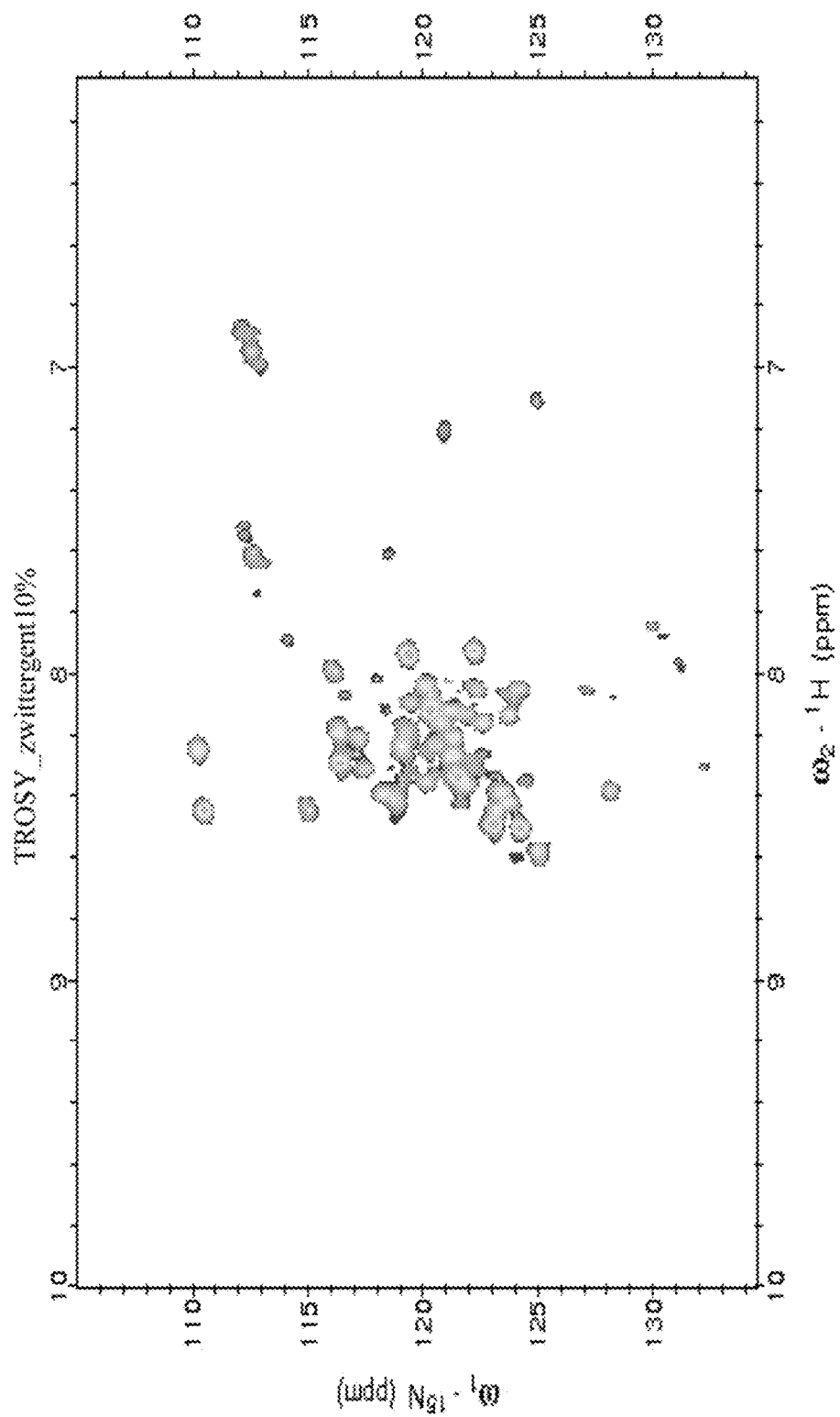
Figure 4E:
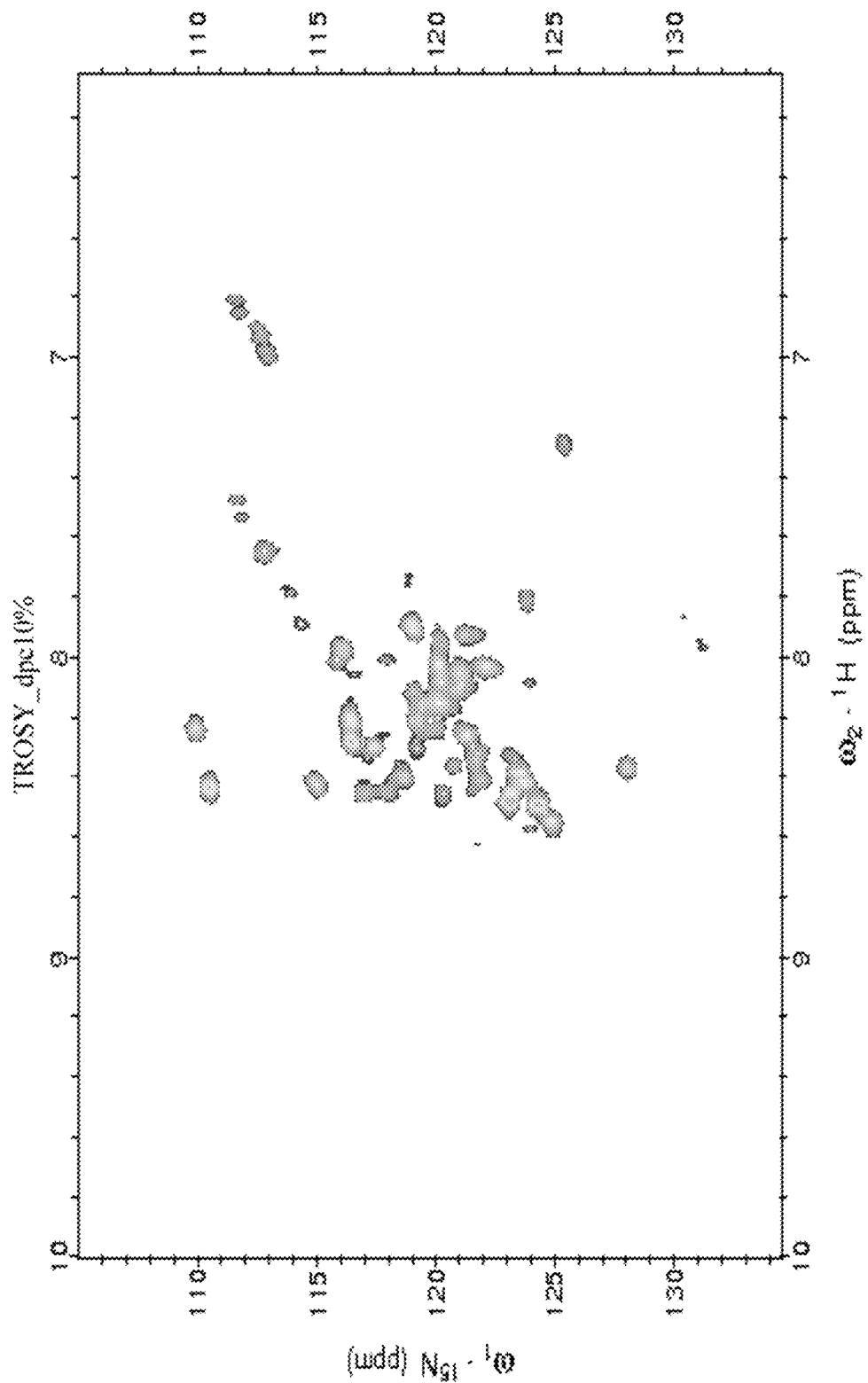

As shown in FIGS. 3 and 4, the SPP-NMR system allows for screening different detergent conditions without purifying the $^{15}$N-enriched target protein to identify those which provide the best quality HSQC (FIG. 3) or TROSY-HSQC (FIG. 4) spectra. The TROSY-HSQC experiment, which has sharper line shapes for relatively slowly tumbling systems like these micelle-solubilized membrane proteins, is the preferred implementation.

The high quality of these TROSY-HSQC spectra suggest it will be possible to determine complete backbone resonance assignments for membrane proteins without further purification using $^{15}$N—$^{1}$H-detected $^{2}$H-decoupled triple resonance experiments (Gardner, K. H., Rosen, M. K., and Kay, L. E. (1997). *Global folds of highly deuterated, methyl-protonated proteins by multidimensional NMR*. Biochemistry 36, 1389-1401; Shan, X., Gardner, K. H., Muhandiram, D. R., Kay, L. E., and Arrowsmith, C. H. (1998). *Subunit-specific backbone NMR assignments of a 64 kDa trp repressor/DNA complex: a* role for N-terminal residues in tandem binding. J Biomol NMR 11, 307-318). The production of such spectra for $^{15}$N-enriched proteins in micelles has not previously been possible. Backbone resonance assignments obtained in this manner would provide the locations of alpha helical and beta strands in the integral membrane protein structure.

The high quality of these TROSY-HSQC spectra suggest it will be possible to determine extensive backbone and sidechain resonance assignments for membrane proteins without further purification, using $^{15}$N—$^{1}$H-detected $^{2}$H-decoupled triple resonance experiments (Gardner, K. H., Rosen, M. K., and Kay, L. E. (1997). *Global folds of highly deuterated, methyl-protonated proteins by multidimensional NMR.* Biochemistry 36, 1389-1401; Shan, X., Gardner, K. H., Muhandiram, D. R, Kay, L. E., and Arrowsmith, C. H. (1998). *Subunit-specific backbone NMR assignments of a 64 kDa trp repressor/DNA complex: a role for N-terminal residues in tandem binding.* J Biomol NMR 11, 307-318).

The high quality of these TROSY-HSQC spectra further suggest it will be possible to determine complete three-dimensional structures of such integral membrane proteins in micelles without protein purification.

These HSQC or TROSY-HSQC spectra can also be used to identify detergents to use in the purification of the target protein, for use in biochemical studies, antibody production, NMR studies, and/or for crystallization and three-dimensional structure determination by X-ray crystallography.

Selective Peptide Bond Labeling With SPP for High Throughput Resonance Assignments Selective labeling of the peptide bond between amino acid residue X and amino acid residue Y (where each of X and Y are any of the 20 common L amino acids) in the sequence X-Y is provided by enriching the protein with amino acid X that is $^{13}$C-enriched in its backbone carbonyl position and amino acid Y that is $^{15}$N-enriched in its backbone $^{15}$N atom. Thus, in a protein sequence, only the X-Y dipeptide sites will have $^{13}$C—$^{15}$N labeled peptide bonds. These sites can be selectively observed using HNCO type triple resonance NMR experiments, providing site-specific resonance assignments of the $^{15}$N, $^{13}$C, and $^{1}$H atoms of the peptide bond, as well as other scalar-coupled or dipolar-coupled atoms. This Peptide Bond Labeling (PBL) approach has been demonstrated using classical *E. coli* expression as well as using cell-free protein expression systems.

SPP-NMR with condensed fermentation is ideally suited for the PBL approach. This method may be referred to as Single Protein Production-Peptide Bond Labeling (hereinafter "SPP-PBL").

Using a robotic protein sample preparation platform (Acton et al, 2005) SPP-PBL can also be implemented in 96-well format. Using this approach, a series of 96 protein samples can be generated, each with a different peptide bond labeled. HNCO (or other NMR experiments) can be recorded on as little as 10 micrograms of these protein samples using 1 mm microNMR probes and a robotic sample changer. In this way, backbone resonance assignments can be obtained for 96 distinct sites in the protein structure.

This SPP-PBL technology is valuable for determining backbone resonance assignments in soluble or membrane proteins, and particularly in perdeuterated membrane proteins. The information provided is valuable for drug design and structure-function studies of proteins.

EXAMPLES

Example 1

$^{15}$N—$^{1}$H HSQC spectra was measured with non-purified, $^{15}$N-labeled RAMP-4 in (A) 10% (vol/vol) bddm (B) 5% (vol/vol) bddm (C) 10% (vol/vol) ldao (D) 10% (vol/vol) zwittergent and (E) 10% DPC (vol/vol) micelles. All the spectra were collected on 800 MHz Bruker US2 spectrometer with cryoprobe at 20 degrees. The samples were prepared in the buffer of 10 mM sodium phosphate, 75 mM sodium chloride, 50 µM EDTA, 5% D$_2$O at pH 7.5. The protein concentration was 200 µM. The spectra with different detergents were recorded and processed in the same manner. The measuring time for each spectrum was four and half hours. See FIG. 3.

Example 2

$^{15}$N—$^{1}$H TROSY spectra measured with non-purified, $^{15}$N-labeled RAMP-4 in (A) 10% (vol/vol) bddm (B) 5% (vol/vol) bddm (C) 10% (vol/vol) ldao (D) 10% (vol/vol) zwittergent and (E) 10% DPC (vol/vol) micelles. Sample preparations and the NMR instrument used for data collection were the same as in Example 1. The spectra with different detergent conditions were recorded and processed identically. The data collection time for each spectrum was nine and half hours. See FIG. 4.

What is claimed:

1. A method of separately inducing a target protein in a living cell comprising:
   i. providing an isolated living cell having a mRNA sequence;
   ii. providing a vector comprising a promoter-operator region of tetA$^{PO}$ and tetR genes from Tn10; a multiple cloning site downstream of the tetA$^{PO}$ gene; and mutated nucleic acid sequences encoding the mRNA interferase polypeptide which produces mRNA free from the nucleotide sequence ACA, and the target protein under the controls of the E. coli lac promoter;
   iii. transforming the isolated living cell by introducing the vector into the isolated living cell;
   iv. contacting the transformed isolated living cell with tetracycline to induce only the mRNA interferase polypeptide thereby inducing the mRNA interferase polypeptide; and
   v. contacting the transformed isolated living cell with IPTG to induce the target protein after the induction of the mRNA interferase polypeptide, thereby separately inducing the target protein.

2. The method of claim 1, wherein the interferase polypeptide is mazF.

3. The method of claim 1, wherein the mRNA encoding the background proteins are consumed upon the induction of the mRNA interferase polypeptide, and wherein the method further comprises the step of eliminating the mRNA encoding the background protein before contacting the transformed isolated living cell with IPTG.

4. The method of claim 1, further comprising the step of contacting the transformed cell with an isotope-enriched media after the induction of the mRNA interferase polypeptide.

5. The method of claim 4, wherein the isotope-enriched media comprises $^2$H-isotopes to produce a $^2$H-enriched protein.

6. The method of claim 4 wherein the isotope-enriched media comprises $^2$H, $^{15}$N, $^{13}$C isotopes to produce a $^2$H, $^{15}$N, $^{13}$C-enriched protein.

7. The method of claim 6, wherein the isotope-enriched media further comprises isotopes selected from the group consisting of $^{13}$C—$^1$H labeled methyls, $^{12}$C-$^1$H labeled methyls, $^{13}$C—$^1$H labeled aromatic side chains, $^{12}$C—$^1$H labeled aromatic side chains and mixtures thereof.

8. The method of claim 4, wherein the isotope-enriched media comprises $^{13}$C—$^{15}$N peptide bond isotopes to produce a $^{13}$C—$^{15}$N peptide bond labeled protein.

9. The method of claim 4, wherein the isotope-enriched media comprises $^{15}$N isotopes to produce a $^{15}$N-enriched protein.

* * * * *

UNITED STATES PATENT AND TRADEMARK OFFICE
CERTIFICATE OF CORRECTION

PATENT NO. : 8,450,085 B2  
APPLICATION NO. : 12/531447  
DATED : May 28, 2013  
INVENTOR(S) : Gaetano T. Montelione et al.

Page 1 of 1

It is certified that error appears in the above-identified patent and that said Letters Patent is hereby corrected as shown below:

In the Specification

Column 1 Lines 14-15, Delete the Statement Regarding Federally Sponsored Research and replace with:
"This invention was made with government support under grant number GM074958 awarded by the National Institutes of Health. The government has certain rights in the invention."

Signed and Sealed this
Ninth Day of June, 2020

Andrei Iancu
*Director of the United States Patent and Trademark Office*